(12) United States Patent
Min et al.

(10) Patent No.: US 8,244,375 B2
(45) Date of Patent: Aug. 14, 2012

(54) MRI COMPATIBLE LEAD

(75) Inventors: Xiaoyi Min, Thousand Oaks, CA (US);
J. Christopher Moulder, Lake Balboa, CA (US); Yong D. Zhao, Simi Valley, CA (US); Kevin L. Morgan, Simi Valley, CA (US); Martin Cholette, Acton, CA (US); Phong D. Doan, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 508 days.

(21) Appl. No.: 12/197,957

(22) Filed: Aug. 25, 2008

(65) Prior Publication Data

US 2010/0049290 A1  Feb. 25, 2010

(51) Int. Cl.
*A61N 1/05* (2006.01)
(52) U.S. Cl. ........................................ 607/122; 607/116
(58) Field of Classification Search ........... 607/116–122
See application file for complete search history.

(56) References Cited

U.S. PATENT DOCUMENTS

| | | | |
|---|---|---|---|
| 5,052,404 A | 10/1991 | Hodgson | |
| 5,222,506 A * | 6/1993 | Patrick et al. | 607/126 |
| 5,824,026 A | 10/1998 | Diaz | |
| 6,697,675 B1 * | 2/2004 | Safarevich et al. | 607/116 |
| 6,949,929 B2 | 9/2005 | Gray et al. | |
| 6,985,775 B2 | 1/2006 | Reinke et al. | |
| 7,013,180 B2 | 3/2006 | Villaseca et al. | |
| 7,015,393 B2 | 3/2006 | Weiner et al. | |
| 7,123,013 B2 | 10/2006 | Gray | |
| 7,174,219 B2 | 2/2007 | Wahlstrand et al. | |
| 2003/0083723 A1 | 5/2003 | Wilkinson et al. | |
| 2003/0083726 A1 | 5/2003 | Zeijlemaker et al. | |
| 2003/0144716 A1 | 7/2003 | Reinke et al. | |
| 2003/0144718 A1 | 7/2003 | Zeijlemaker | |
| 2003/0144719 A1 | 7/2003 | Zeijlemaker | |
| 2003/0144720 A1 | 7/2003 | Villaseca et al. | |
| 2003/0144721 A1 | 7/2003 | Villaseca et al. | |
| 2005/0222647 A1 | 10/2005 | Wahlstrand et al. | |
| 2005/0222657 A1 | 10/2005 | Wahlstrand et al. | |
| 2005/0222659 A1 | 10/2005 | Olsen et al. | |
| 2006/0030774 A1 | 2/2006 | Gray et al. | |
| 2006/0200218 A1 | 9/2006 | Wahlstrand | |
| 2007/0179577 A1 | 8/2007 | Marshall et al. | |
| 2008/0243218 A1 | 10/2008 | Bottomley et al. | |

FOREIGN PATENT DOCUMENTS

| | | |
|---|---|---|
| EP | 1469910 B1 | 12/2006 |
| WO | 03063952 A2 | 8/2003 |
| WO | 03063952 A3 | 8/2003 |
| WO | 03063955 A1 | 8/2003 |

(Continued)

OTHER PUBLICATIONS

WO 03063957 A3-Search, Aug. 7, 2003, Zeijemaker.

(Continued)

*Primary Examiner* — Niketa Patel
*Assistant Examiner* — Joseph Stoklosa

(57) ABSTRACT

Disclosed herein is an implantable medical lead. In one embodiment, the lead includes a ring electrode, a tip electrode, first and second helically wound coaxial conductor coils, and a distal coil transition. The coils extend between the proximal and distal ends of the lead. The distal coil transition is proximal to the ring electrode and near the distal end and is where the first coil transitions from being outside the second coil proximal of the distal coil transition to being inside the second coil distal of the distal coil transition.

7 Claims, 3 Drawing Sheets

FOREIGN PATENT DOCUMENTS

| | | | |
|---|---|---|---|
| WO | 03063957 | A2 | 8/2003 |
| WO | 2005102446 | A1 | 11/2005 |
| WO | 2005102447 | A1 | 11/2005 |
| WO | 2006093685 | A1 | 9/2006 |
| WO | 2007047966 | A2 | 4/2007 |
| WO | 2007047966 | A3 | 4/2007 |
| WO | 2007089988 | A1 | 8/2007 |

OTHER PUBLICATIONS

WO 03063957 A3-AmendClm, Aug. 7, 2003, Zeijemaker.

* cited by examiner

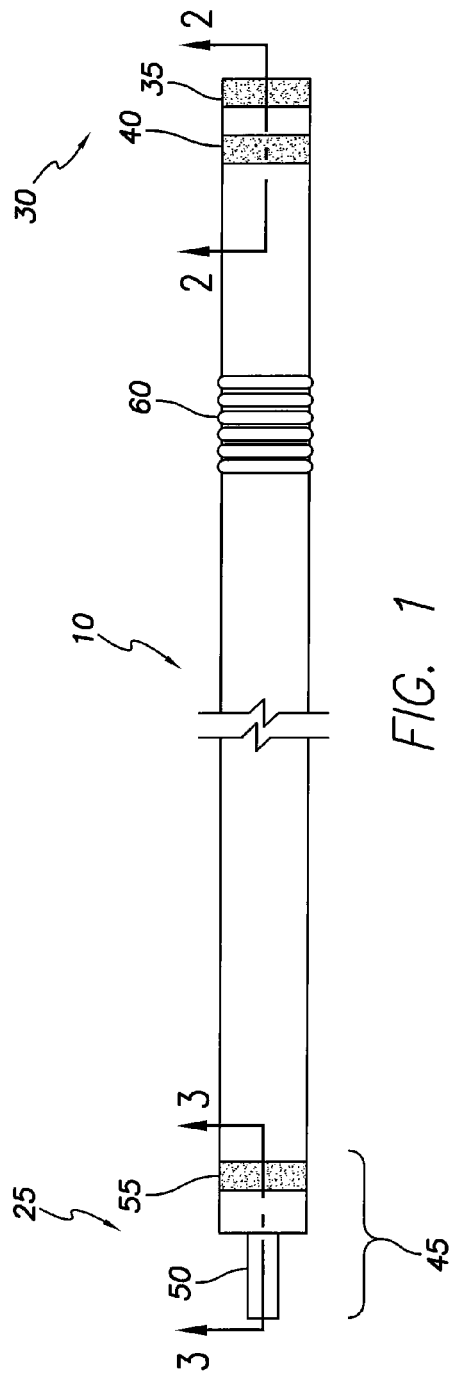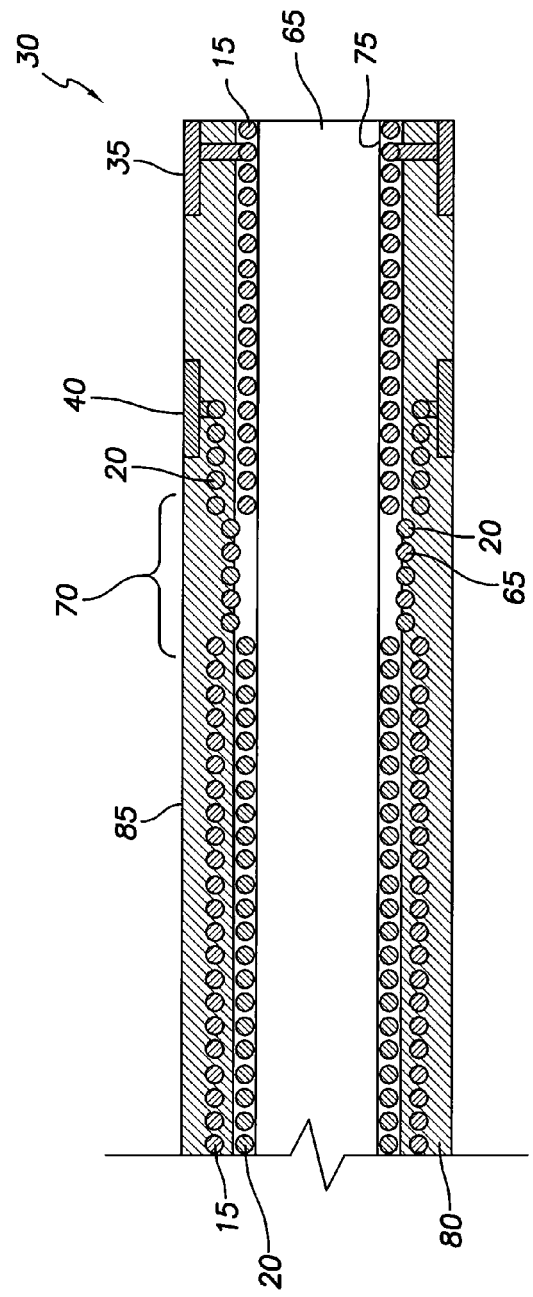

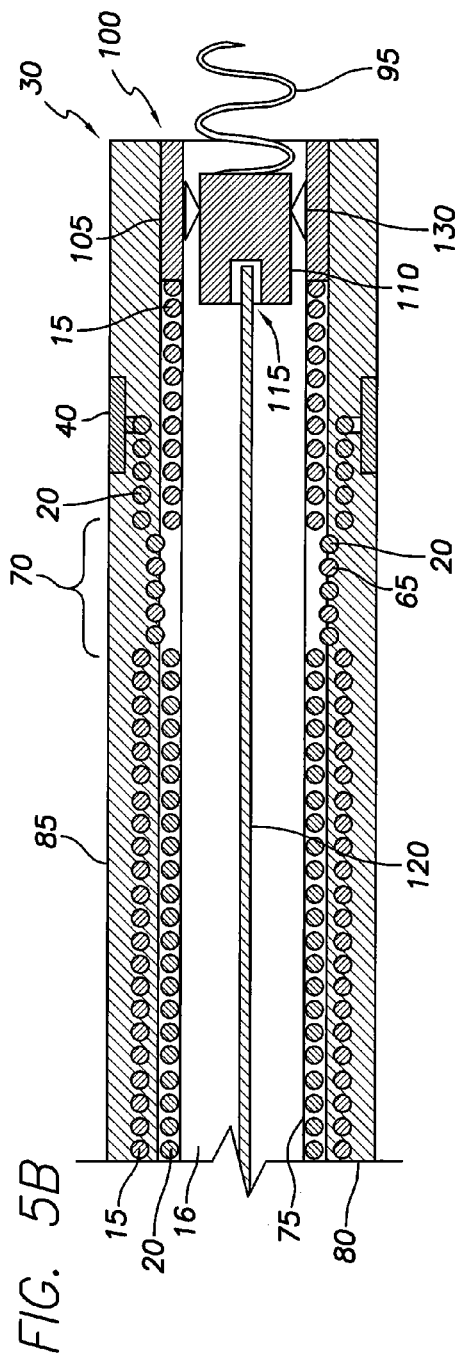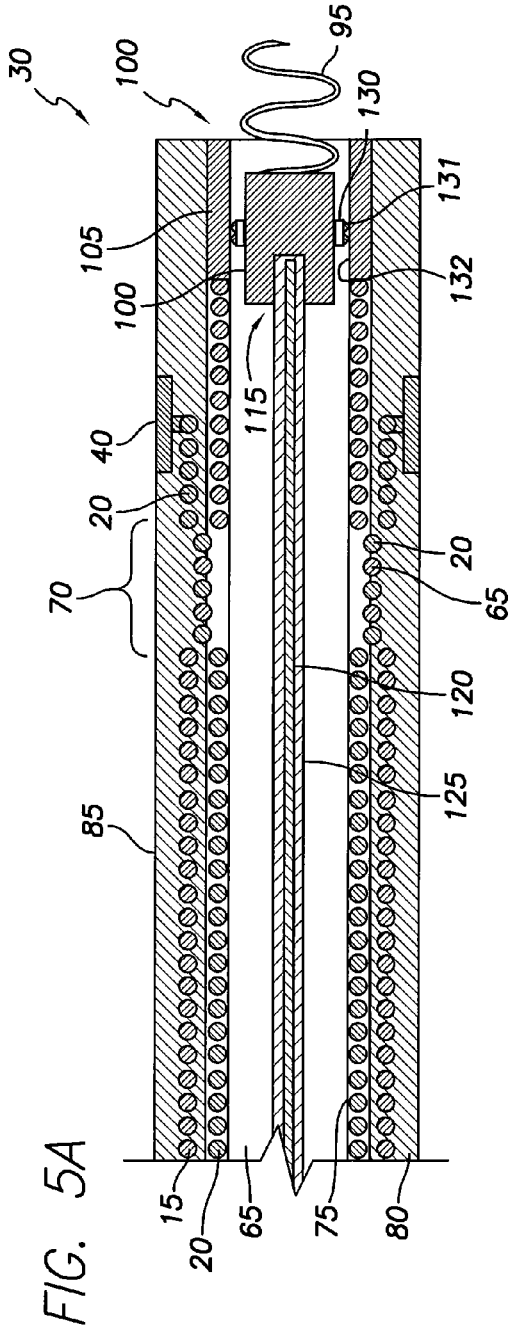

MRI COMPATIBLE LEAD

FIELD OF THE INVENTION

The present invention relates to implantable medical leads. More specifically, the present invention relates to implantable medical leads compatible with magnetic resonance imaging ("MRI").

BACKGROUND OF THE INVENTION

There is concern in the medical community regarding the potential harm a MRI can cause to a patient having one or more implanted medical leads. Conductors extending through an implantable medical lead can act as an antenna when located in a RF field generated by MRI. The energy absorbed by the conductors can cause the electrodes connected to the conductors to heat up, potentially damaging the tissue contacting the electrodes. The damaged tissue can then become ineffective for pacing or sensing purposes.

For patients having implanted medical leads, it would be beneficial to be able to utilize MRI for diagnosis of medical conditions without a risk of lead electrode heating.

There is a need in the art for a MRI compatible implantable medical lead. There is also a need in the art for a method of manufacturing such a lead.

SUMMARY

Disclosed herein is an implantable medical lead having a proximal end and a distal end. In one embodiment, a first helically wound conductor coil, a second helically wound conductor coil, a ring electrode and a tip electrode. The first coil extends between the proximal and distal ends. The second coil extends between the proximal and distal ends and extends about the first coil in a coaxial configuration for at least a portion of the lead. The ring electrode is electrically coupled to the first coil. The tip electrode is electrically coupled to the second coil.

Disclosed herein is an implantable medical lead. In one embodiment, the lead includes a ring electrode, a tip electrode, first and second helically wound coaxial conductor coils, and a distal coil transition. The coils extend between the proximal and distal ends of the lead. The distal coil transition is proximal to the ring electrode and near the distal end of the lead and is where the first coil transitions from being outside the second coil proximal of the distal coil transition to being inside the second coil distal of the distal coil transition.

Disclosed herein is an implantable medical lead. In one embodiment, the lead includes a lead body and an anchor distal tip electrode. The lead body includes a first helical conductor coil extending longitudinally through the lead body. The anchor distal tip electrode is electrically coupled to the first helical conductor coil and rotatable relative to the first conductor coil.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 is a side view of an implantable medical lead.
FIG. 2 is a longitudinal cross-section of the lead distal end as taken along section line 2-2 in FIG. 1
FIG. 5A is a longitudinal cross-section of the lead distal end as taken along section line 5-5 in FIG. 4.
FIG. 5B is the same view as FIG. 5A, except of an embodiment having a central tubing and a different mechanical connection at the distal end for the anchor electrode.

DETAILED DESCRIPTION

Figure 3:
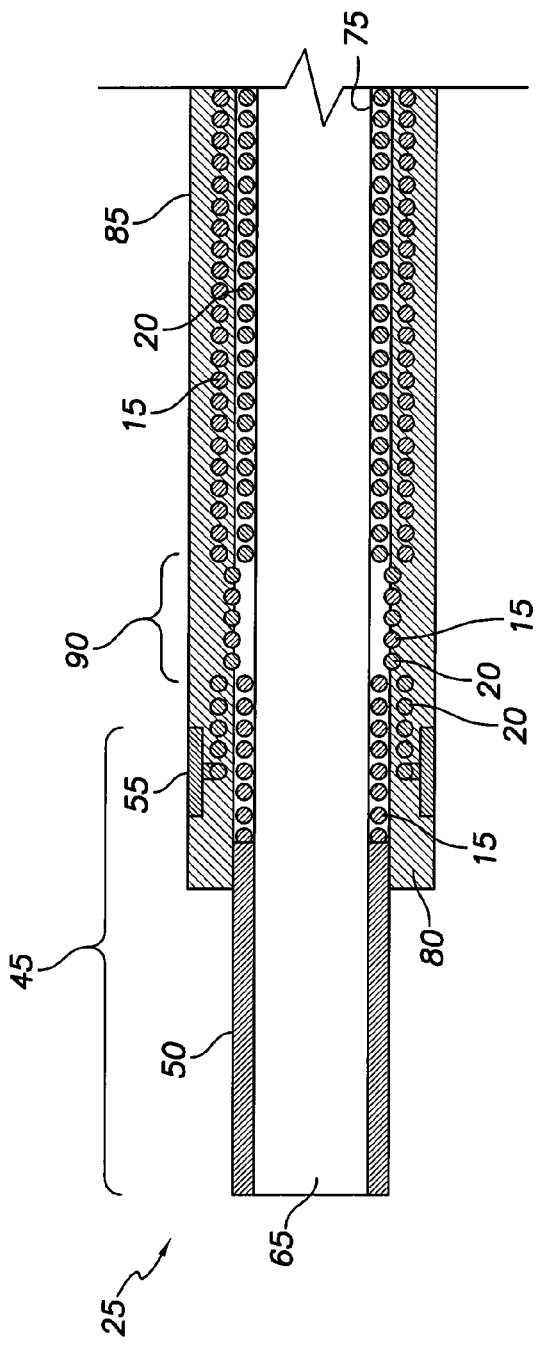
FIG. 3 is a longitudinal cross-section of the lead proximal end as taken along section lines 3-3 in FIGS. 1 and 4.

Disclosed herein are implantable medical leads 10 that are compatible with MRI. In one embodiment, a lead 10 includes first and second helically wound conductor coils 15, 20 extending between proximal and distal ends 25, 30 of the lead. The lead 10 also includes tip and ring electrodes 35, 40 near the distal end 30.

The first coil 15 is outer relative to the second coil 20 over the majority of the length of the lead 10. Near the distal end 30, the coils 15, 20 transition such that the second coil 20 becomes outer relative to the first coil 15. The first coil 15 is electrically connected to the tip electrode 35, and the second coil 20 is electrically connected to the ring electrode 40. Since the tip electrode 35 is electrically connected to the first coil 15, which is the outer coil for the majority of the length of the lead 10, the tip electrode 35 is electrically connected to the coil having the largest diameter of the two coils 15, 20 for the greatest extent of the lead length. The larger diameter results in greater inductance in the coil connected to the tip electrode 35, thereby reducing the magnitude of electrode heating associated with the tip electrode 35.

For a discussion regarding a first lead embodiment, reference is made to FIG. 1, which is a side view of an implantable medical lead 10. As shown in FIG. 1, the lead 10 includes a proximal end 25 and a distal end 30 and may be configured for passive fixation. The distal end 30 may include a tip electrode 35 and one or more ring electrodes 40. The proximal end 25 may include a lead connector end 45 for mechanically and electrically coupling the proximal end 25 to a pulse generator, such as a pacemaker or implantable cardioverter defibrillator ("ICD"). The lead connector end 45 may be an IS-1 or other type of connector end that includes a contact pin 50 and one or more contact rings 55. The contact pin 50 and contact ring(s) 55 make electrical contact with corresponding structures within the pulse generator when the lead connector end 45 is received in the pulse generator. Proximal of the distal end 30, the lead 10 may include a defibrillation coil 60.

As indicated in FIG. 2, which is a longitudinal cross-section of the lead distal end 30 as taken along section line 2-2 in FIG. 1, the lead 10 may include a central lumen 65, a first helically wound conductor coil 15, a second helically wound conductor coil 20, a distal coil transition 70, a lumen liner 75, and an outer layer 80. The outer layer 80 forms the wall of the lead 10 and the outer circumferential surface 85 of the lead 10. The outer layer 80 may be formed of materials such as silicone rubber, polyurethane, or silicone rubber—polyurethane—copolymer ("SPC").

When present, the lumen liner 75 will form the inner circumferential surface of the central lumen 65, which extends between the proximal and distal ends 25, 30 of the lead 10. Delivery tools, such as stylets or guidewires, can be extended through the lumen 65 to assist in delivery of the lead distal end 30 to the implant site within the patient. The lumen liner 75 may be formed of polytetrafluoroethylene ("PTFE") or other polymer materials having a low coefficient of friction.

The first and second coils 15, 20 may each be multi-filar helically wound coils. The coils 15, 20 may be co-radial or co-axial relative to each other. In one embodiment, each coil 15, 20 is electrically insulated with its own respective insulation jacket. In another embodiment, only one of the coils 15, 20 is electrically insulated with an insulation jacket. The insulation for a coil 15, 20 may be a jacket or coating that is common to two or more filar conductive cores, or the insulation for a coil 15, 20 may be a jacket or coating that insulates a single filar conductive core (i.e., each filar conductive core has its own respective insulation jacket or coating).

The second coil 20 proximal of the transition 70 extends about the inner circumferential surface of the outer layer 80. The second coil 20 extends about the outer circumferential surface of the lumen liner 75 where the lead 10 includes such a liner 75. If the lead 10 does not include the lumen liner 75, the second coil 20 will act as the inner circumferential surface of the lumen 65.

Proximal of the distal transition 70, the first coil 15 extends about the second coil 20 and is imbedded in the outer layer 80. Distal of the distal transition 70, the second coil 20 extends about the first coil 15 and is imbedded in the outer layer 80. The transition 70 is where the filars of the first coil 15 passes through the filars of the second coil 20 such that the coils 15, 20 can radially or co-axially switch position relative to each other. Distal the distal transition 70, the second coil 20 electrically connects to the ring electrode 40 and the first coil 15 electrically connects to the tip electrode 35.

In one embodiment, as can be understood from FIG. 2, the coils 15, 20 are coaxially arranged and in radially close proximity to each other such that the inner circumferential surface of one coil is near, or even touches, the outer circumferential surface of the other coil, thereby reducing the diameter needed for the lead body to have a coaxial coil configuration. In one embodiment, the single first coil 15 may be replaced with multiple coaxial coils (e.g., the first coil 15 is replaced with two, three, or more coaxial coils) in a radially close or radially touching arrangement, and/or the single second coil 20 may be replaced with multiple coaxial coils (e.g., the second coil 20 is replaced with two, three, or more coaxial coils) in a radially close or radially touching arrangement.

As illustrated in FIG. 3, which is a longitudinal cross-section of the lead proximal end 25 as taken along section line 3-3 in FIG. 1, in some embodiments, the lead 10 will also include a proximal transition 90 in addition to the distal transition 70 depicted in FIG. 2. Accordingly, as with the distal transition 70, the proximal transition 90 is where the filars of the first coil 15 passes through the filars of the second coil 20 such that the coils 15, 20 can radially or co-axially switch position relative to each other. Distal the proximal transition 90, the first coil 15 extends about the second coil 20 and is imbedded in the outer layer 80. Proximal the proximal transition 90, the second coil 20 extends about the first coil 15 and is imbedded in the outer layer 80. Proximal the proximal transition 90, the second coil 20 electrically connects to the contact ring 55 of the lead connector end 45 and the first coil 15 electrically connects to the contact pin 50 of the lead connector end 45.

While the proximal transition 90 is not necessary, it is advantageous in that it allows the lead connector end 45 to be electrically compatible with standard pulse generators, which are configured to connect to lead connector ends 45 such as an IS-1 or other types of lead connector ends 45 having a contact pin 50 electrically connected to a tip electrode and contact ring(s) 55 electrically connected to ring electrode(s).

As can be understood from FIGS. 2 and 3, between the distal and proximal transition 70, 90, the first coil 15 extends about the second coil 20 and is imbedded in the outer layer 80. Despite being the conductor coil 15 electrically connected to the tip electrode 35 and, in some instances, the contact pin 50, the first conductor coil 15 is routed through the lead 10 to be the radially outer coil for a substantial majority of the length of the lead 10. Thus, the tip electrode 35 is less likely to heat up when the lead 10 is present in an RF field due to the increased inductance provided by the increased diameter of the first coil 15.

Figure 4:
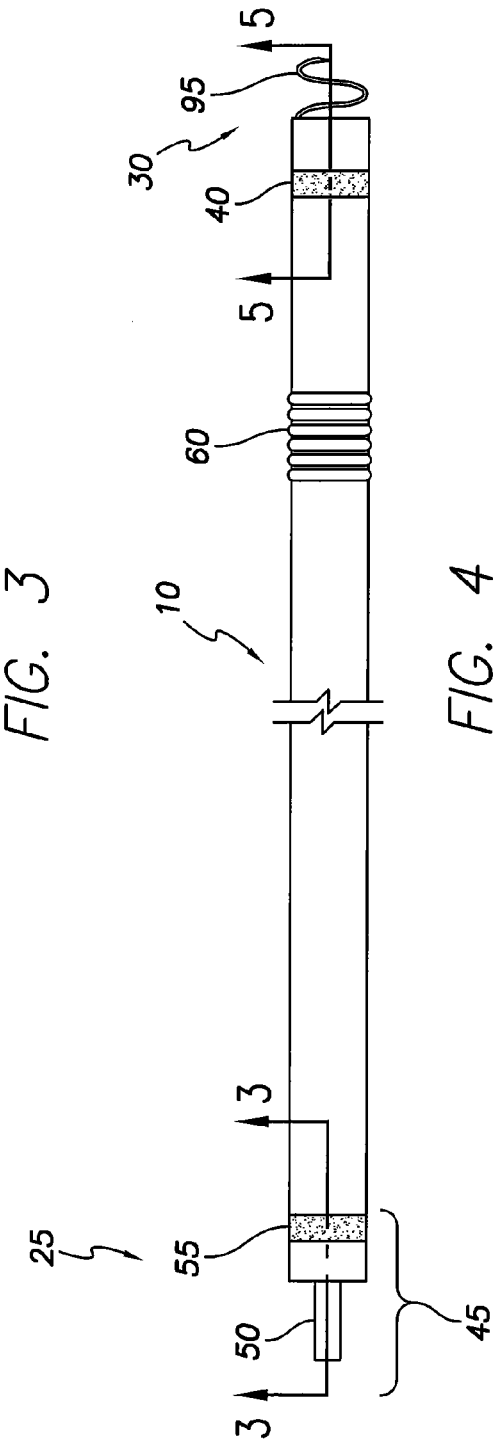
FIG. 4 is a side view of an implantable medical lead.

For a discussion regarding a second lead embodiment, reference is made to FIG. 4, which is a side view of an implantable medical lead 10. As shown in FIG. 4, the lead 10 includes a proximal end 25 and a distal end 30 and may be configured for active fixation. The distal end 30 may include one or more ring electrodes 40 and a tip electrode 95 in the form of a helical anchor 95. The proximal end 25 may include a lead connector end 45 as discussed above with respect to FIGS. 1 and 3.

As indicated in FIG. 5A, which is a longitudinal cross-section of the lead distal end 30 as taken along section line 5-5 in FIG. 4, the lead 10 may include a central lumen 65, a first helically wound conductor coil 15, a second helically wound conductor coil 20, a distal coil transition 70, a lumen liner 75, an outer layer 80, and a mechanical contact 100. The outer layer 80 forms the wall of the lead 10 and the outer circumferential surface 85 of the lead 10. The outer layer 80 may be formed of materials such as silicone rubber, polyurethane, or SPC.

When present, the lumen liner 75 will form the inner circumferential surface of the central lumen 65, which extends between the proximal and distal ends 25, 30 of the lead 10. Delivery tools, such as stylets or guidewires, can be extended through the lumen 65 to assist in delivery of the lead distal end 30 to the implant site within the patient. The lumen liner 75 may be formed of PTFE or other polymer materials having a low coefficient of friction.

The first and second coils 15, 20 may each be multi-filar helically wound coils. The coils 15, 20 may be co-radial or co-axial relative to each other. In one embodiment, each coil 15, 20 is electrically insulated with its own respective insulation jacket. In another embodiment, only one of the coils 15, 20 is electrically insulated with an insulation jacket. The insulation for a coil 15, 20 may be a jacket or coating that is common to two or more filar conductive cores, or the insulation for a coil 15, 20 may be a jacket or coating that insulates a single filar conductive core (i.e., each filar conductive core has its own respective insulation jacket or coating).

The second coil 20 proximal of the transition 70 extends about the inner circumferential surface of the outer layer 80. The second coil 20 extends about the outer circumferential surface of the lumen liner 75 where the lead 10 includes such a liner 75. If the lead 10 does not include the lumen liner 75, the second coil 20 will act as the inner circumferential surface of the lumen 65.

Proximal of the distal transition 70, the first coil 15 extends about the second coil 20 and is imbedded in the outer layer 80. Distal of the distal transition 70, the second coil 20 extends about the first coil 15 and is imbedded in the outer layer 80. The transition 70 is where the filars of the first coil 15 passes through the filars of the second coil 20 such that the coils 15, 20 can radially or co-axially switch position relative to each other. Distal the distal transition 70, the second coil 20 electrically connects to the ring electrode 40 and the first coil 15 electrically connects to the mechanical contact 100, which is electrically connected to the helical anchor electrode 95.

In one embodiment, as can be understood from FIG. 5A, the coils 15, 20 are coaxially arranged and in radially close proximity to each other such that the inner circumferential surface of one coil is near, or even touches, the outer circumferential surface of the other coil, thereby reducing the diameter needed for the lead body to have a coaxial coil configuration. In one embodiment, the single first coil 15 may be replaced with multiple coradial coils (e.g., the first coil 15 is replaced with two, three, or more coradial coils) in a radially close or radially touching arrangement, and/or the single second coil 20 may be replaced with multiple coradial coils (e.g., the second coil 20 is replaced with two, three, or more coradial coils) in a radially close or radially touching arrangement.

As shown in FIG. 5A, in one embodiment, the mechanical contact 100 includes an inner ring 105 and a rotational member 110. The inner ring 105 electrically connects with the first coil 15 and forms the inner circumferential surface of the lumen 65 near the extreme distal end of the lumen 65. The rotational member 110 is electrically connected to the helical anchor electrode 95 and includes an opening 115 in the proximal face of the member 110. The opening 115 is for receiving therein a stylet 120 for rotating the member 110 relative to the rest of the inner ring 105. As can be understood from FIGS. 5A and 5B, the member 110 and helical anchor electrode 95 can be rotated relative to the rest of the lead body and, more particularly, relative to both coils 15, 20.

In one embodiment, in addition to being electrically connected to each other, the rotation member 110 and inner ring 105 are threadably or otherwise engaged with each other such that rotation of the member 110 relative to the inner ring 105 causes the anchor electrode 95 to extend from, or retract into, the lead lumen 65, depending on the direction of rotation.

The inner ring 105 and rotation member 110 are formed of an electrically conductive, biocompatible material such as Pt/Ir Alloy, stainless steel, etc.

As can be understood from FIG. 5B, which is the same view as FIG. 5A, except of an embodiment having a central tubing 125, the central tubing 125 leads from the contact pin 50 to the opening 115. The central tubing 125 guides the stylet 120 to the opening so the stylet can be used to rotate the anchor electrode 95 into or out of tissue. The stylet 120 can be a screw driver type of stylet having a distal end capable of engagement with the opening 115 so as to transfer torque from lead proximal to distal and screw the helix 95 into the heart muscle at a desired location.

As can be understood from FIG. 5A, in one embodiment, the necessary electrical contact pressure between the ring 105 and the member 110 is achieved by providing a biasing structure (e.g., a spring) 130 between the engaging surface or features (e.g., threads) of the member 110 and the rest of the member 110. The biasing structure biases the threads 131 into good electrical contact with the corresponding engaging surface 132 or features (e.g., threads) of the ring 105.

As can be understood from FIG. 5B, in one embodiment, the necessary electrical contact pressure between the ring 105 and the member 110 is achieved by providing a biasing structure (e.g., a spring) 130 between the member 110 and the ring 105. In such an embodiment, the biasing structure 130 also serves as the engaging features (e.g., threads) of the ring 105 to engage in good electrical contact the corresponding engaging features of the member 110.

As illustrated in FIG. 3, which is a longitudinal cross-section of the lead proximal end 25 as taken along section line 3-3 in FIG. 4, in some embodiments, the lead 10 will also include a proximal transition 90 in addition to the distal transition 70 depicted in FIG. 5A. Accordingly, as with the distal transition 70, the proximal transition 90 is where the filars of the first coil 15 passes through the filars of the second coil 20 such that the coils 15, 20 can radially or co-axially switch position relative to each other. Distal the proximal transition 90, the first coil 15 extends about the second coil 20 and is imbedded in the outer layer 80. Proximal the proximal transition 90, the second coil 20 extends about the first coil 15 and is imbedded in the outer layer 80. Proximal the proximal transition 90, the second coil 20 electrically connects to the contact ring 55 of the lead connector end 45 and the first coil 15 electrically connects to the contact pin 50 of the lead connector end 45.

While the proximal transition 90 is not necessary, it is advantageous in that it allows the lead connector end 45 to be electrically compatible with standard pulse generators, which are configured to connect to lead connector ends such as an IS-1 or other types of lead connector ends 45 having a contact pin 50 electrically connected to a tip electrode and contact ring(s) 55 electrically connected to ring electrode(s).

As can be understood from FIGS. 5A, 5B and 3, between the distal and proximal transition 70, 90, the first coil 15 extends about the second coil 20 and is imbedded in the outer layer 80. Despite being the conductor coil 15 electrically connected to the helical anchor electrode 95 and, in some instances, the contact pin 50, the first conductor coil 15 is routed through the lead 10 to be the radially outer coil for a substantial majority of the length of the lead 10. Thus, the helical anchor electrode 95 is less likely to heat up when the lead 10 is present in an RF field due to the increased inductance provided by the increased diameter of the first coil 15.

In one embodiment, the leads 10 depicted in FIGS. 1-5B are manufactured as follows. Filars are wound to form coils 15, 20 of different diameters. The filars of one or both coils 15, 20 may be insulated wire. During the coil winding process, the filars of the coils 15, 20 in the transition regions 70, 90 are interwound to allow the coils 15, 20 to radially exchange positions relative to each other along the length of the lead 10.

For the embodiment depicted in FIGS. 3-5B, coil 15 is welded to the inner ring 105 at the lead distal end 30 and to the contact pin 50 of the lead connector end 45 at the lead proximal end 25. For the embodiment depicted in FIGS. 1-3, coil 15 is welded to the tip electrode 35 at the lead distal end 30 and to the contact pin 50 of the lead connector end 45 at the lead proximal end 25. For the embodiments depicted in FIGS. 1-5B, coil 20 is welded to the ring electrode 40 at the lead distal end 30 and to the contact ring 55 of the lead connector end 45 at the lead proximal end 25.

Once the coils 15, 20 are welded to their respective components as described above, an insulation polymer, such as silicone rubber, polyurethane, silicone rubber-polyurethane-copolymer ("SPC or Optim®") is reflowed about the coils and connected components to form an insulated sheath or tubing 85 for the lead 10.

For the embodiment depicted in FIGS. 3-5B, the helix anchor electrode 95 is welded onto the rotational member 110, which is threaded into the inner ring 105. A stopper having an inner diameter larger than the outer diameter of the anchor 95 but smaller than the outer diameter of the member 110 is welded or otherwise joined to the distal end of the inner ring 105 to prevent the rotational member 110 from being distally threaded out of the inner ring 105.

In another embodiment, the leads depicted in FIGS. 1-5B are manufactured as follows. Coil 20 is first wound around a mandrel in a coil winding process. Coil 20 is then subjected to a reflow process that adds about coil 20 a polymeric layer such as silicone rubber, polyurethane, SPC or Optim®. Coil 15 is then wound around the assembly comprising coil 20 and the aforementioned polymeric layer to create the two layers of conducting coils. During this second winding process, the proximal and distal ends of the coils 15, 20 are co-radially formed creating the transition zones 70 and 90. The components of the lead connector end 45 are welded to the proximal ends of the respective coils 15, 20, and the electrode components at the lead distal end 30 are welded to the distal ends of the respective coils 15, 20. This assembly is then subjected to another reflow process that adds the final polymeric layer 80 as described above.

Although the present invention has been described with reference to preferred embodiments, persons skilled in the art will recognize that changes may be made in form and detail without departing from the spirit and scope of the invention.

What is claimed is:

1. An implantable medical lead comprising:
    a first helically wound conductor coil extending between a proximal end and a distal end of the implantable lead;
    a second helically wound conductor coil extending between the proximal and distal ends;
    a ring electrode near the distal end and electrically coupled to the first coil;
    a tip electrode near the distal end, distal of the ring electrode, and electrically coupled to the second coil, wherein the second helically wound coil extends about the first helically wound coil for a first portion of the medical lead between the proximal end of the implantable lead and the ring electrode; and
    a distal transition near the distal end of the lead wherein as the first and second helically wound coils extend distally, the first helically wound coil transitions from being inside the second helically wound coil to being outside the second helically wound coil.

2. The lead of claim 1, further comprising a proximal transition near the proximal end of the lead wherein as the first and second coils extend proximally, the first coil transitions from being inside the second coil to being outside the second coil.

3. The lead of claim 2, further comprising a lead connector end including a contact pin electrically connected to the second coil and a contact ring electrically connected to the first coil.

4. The lead of claim 1, wherein the first and second coils are coaxially aligned.

5. The lead of claim 1, wherein the tip electrode is a helical anchor electrode.

6. The lead of claim 5, wherein the helical anchor electrode is extendable from the lead distal end.

7. The lead of claim 6, wherein the helical anchor electrode is rotatable relative to the lead.

* * * * *